United States Patent [19]

Hearon et al.

[11] 3,998,878

[45] Dec. 21, 1976

[54] SELECTIVELY SEPARATING OXALIC, TARTARIC, GLYOXYLIC AND ERYTHRONIC ACIDS FROM AQUEOUS SOLUTIONS CONTAINING THE SAME

[75] Inventors: William Montgomery Hearon, Portland, Oreg.; Cheng Fan Lo; John F. Witte, both of Vancouver, Wash.

[73] Assignee: Boise Cascade, Portland, Oreg.

[22] Filed: Nov. 5, 1975

[21] Appl. No.: 628,888

[52] U.S. Cl. .......................... 260/536; 260/526 R; 260/535 R; 260/538
[51] Int. Cl.² ........................................ C07C 59/14
[58] Field of Search ............... 260/536, 535 R, 538, 260/526 R

[56] References Cited

UNITED STATES PATENTS

| | | | |
|---|---|---|---|
| 2,470,841 | 5/1949 | Barch | 260/536 |
| 2,813,121 | 11/1957 | Makay | 260/536 |
| 3,872,166 | 3/1975 | Spaenig et al. | 260/535 R |

FOREIGN PATENTS OR APPLICATIONS

| | | | |
|---|---|---|---|
| 43,618 | 12/1960 | Poland | 260/536 |
| 50,060 | 12/1965 | Poland | 260/536 |
| 51,151 | 4/1966 | Poland | 260/536 |

*Primary Examiner*—Paul J. Killos
*Attorney, Agent, or Firm*—Eugene D. Farley

[57] ABSTRACT

Mixtures of oxalic, meso tartaric, glyoxylic and erythronic acids derived particularly from the oxidation of cellulose derivatives are separated from aqueous solutions in which they are contained and from each other by stepwise precipitation with calcium ion at controlled pH. The oxalic acid is precipitated as calcium oxalate at a pH of 0.9 to 2.0; the tartaric acid as calcium meso tartrate at a pH of 2.8 to 4.4; and the glyoxylic acid, as calcium glyoxylate at a pH of 4.5 to 5.4. After each precipitation the water insoluble precipitate is separated from the aqueous mixture in which it is contained. The relatively soluble erythronic acid remains in solution as a free acid, or in the form of its calcium salt.

17 Claims, 1 Drawing Figure

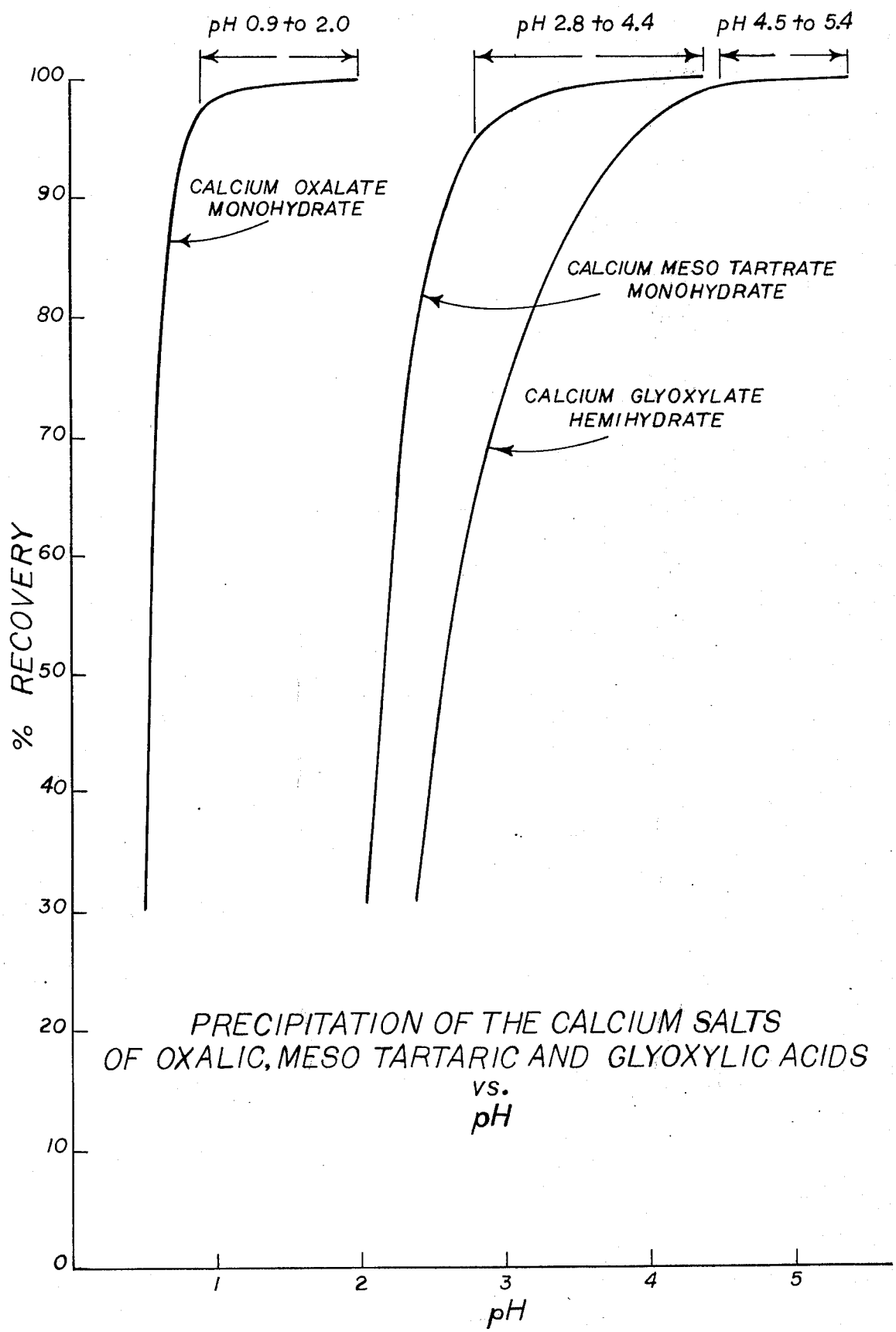

SELECTIVELY SEPARATING OXALIC, TARTARIC, GLYOXYLIC AND ERYTHRONIC ACIDS FROM AQUEOUS SOLUTIONS CONTAINING THE SAME

This invention pertains to a process for the separation and isolation of organic acids from solutions in which they are contained. It pertains particularly to the separation of oxalic, meso tartaric, glyoxylic and erythronic acids, resulting from the oxidation and/or hydrolysis of cellulose derivatives, from each other and from aqueous solutions in which they are contained.

BACKGROUND OF THE INVENTION

Oxalic, tartaric, glyoxylic and erythronic acids are products having large present and potential commercial applications. In theory they are obtainable at low cost and in unlimited quantity from cellulosic raw materials.

In one procedure of potential application it is possible to manufacture these acids from wood or woody materials by (1) converting the material to cellulose e.g. paper pulp, (2) oxidizing the cellulose to dialdehyde cellulose, (3) oxidizing the dialdehyde cellulose to di- and tricarboxy celluloses and (4) hydrolyzing the di- and tricarboxy celluloses to a mixture of oxalic, tartaric, glyoxylic and erythronic acids. A process for effectuating the last of the above named steps is set forth and described in our copending application Ser. No. 628,887 filed Nov. 5, 1975, entitled HYDROLYZING DI- AND TRICARBOXY CELLULOSES WITH SULFUROUS ACID.

In another potentially available process carbohydrate materials are oxidized in aqueous solution by means of an oxidizing agent such as nitric acid, producing a mixture of oxalic, tartaric and other organic acids.

A problem is presented in isolating the individual acids from such mixtures. Prior art procedures for accomplishing this result are outlined in U.S. Pat. Nos. 2,319,020 and 2,470,841. However, such procedures have the common failing of requiring the use of expensive reagents in complicated and time consuming operational sequences. In addition, they do not produce the nearly quantitative yields required for the practical, low cost, commercial production of the organic acids in question.

It accordingly is the general purpose of the present invention to provide an economical, practical, low cost procedure for the substantially quantitative isolation of oxalic, tartaric, glyoxylic and erythronic acids, or any one or ones of such acids, from each other and from aqueous solutions in which they are contained in admixture with each other.

SUMMARY OF THE INVENTION

We now have discovered that oxalic, tartaric, glyoxylic and erythronic acids may be separated substantially quantitatively from each other and from aqueous solutions in which they are contained by taking advantage of the fact that the free acids may be converted to corresponding calcium salts which are characterized by unique degrees of insolubility over limited and progressive pH ranges.

Thus, calcium oxalate is precipitated over a pH range of pH 0.9 to pH 2.0 to the substantial exclusion of the calcium salts of the other three acids. Calcium tartrate is precipitated at a pH range of from pH 2.8 to pH 4.4 to the substantial exclusion of the calcium salts of glyoxylic acid and erythronic acid, while maintaining the solution substantially unsaturated with respect to the latter two acids. Calcium glyoxylate is precipitated at a pH of from pH 4.5 to pH 5.4 while retaining erythronic acid and/or its calcium salt in solution.

Surprisingly, the separation of the acids is free from the complications which normally are to be expected in the execution of a fractionation process such as is outlined above. When operating in the indicated pH ranges, the calcium salts are precipitated almost quantitatively. Additionally, in each case the calcium salt of lesser solubility is substantially uncontaminated by the calcium stals of greater solubility.

Still further, there is avoided the occurrence of undesirable side reactions which would lead to the contamination of the respective products, or to diminution of the yields in which they are obtained.

For example, glyoxylic acid under certain conditions is converted by the Cannizzaro reaction to oxalic acid and glycolic acid. The occurrence of this undesirable side reaction is eliminated completely by carrying out the precipitation of calcium glyoxylate at a pH value of from 4.5 to 5.4. Still further, the acid products are obtained in a pure condition, suitable for commercial use.

DESCRIPTION OF SPECIFIC EMBODIMENTS OF THE INVENTION

The present process is described with particular reference to the drawing comprising graphs illustrating the critical pH ranges characterizing the selective precipitation of calcium oxalate, calcium tartrate and calcium glyoxylate, respectively. In determining the pH values, use was made of a "Corning" model 5 pH meter, a product of Corning Scientific Instruments Co., Corning, New York; and in the lower pH range, of "Hydrion" pH paper having a range of from pH 0.0 to 1.5, a product of Micro Essential Laboratory of Brooklyn, New York.

As noted above, the starting materials for the process of the invention may comprise aqueous solutions of oxalic, tartaric, glyoxylic and erythronic acids, or any one or more of such acids. The tartaric acid is in the form of meso tartaric acid and as used herein, the term "tartaric acid" refers to meso tartaric acid exclusively.

The process of the invention is applicable particularly to the fractionation of the mixture of acids from the oxidation and/or hydrolysis of various cellulose derivatives such as di- and tricarboxyl cellulose obtained by the oxidation of dialdehyde cellulose. When derived from this source, the mixture of acids is obtained as an aqueous solution, and it is this solution which is the starting material for the hereindescribed process.

In the execution of the process, the acids are separated from each other in the order: oxalic acid, tartaric acid, glyoxylic acid and erythronic acid.

Considering first the manner of separation of the oxalic acid:

Separation of Oxalic Acid

The oxalic acid is separated from the solution of mixed acids in the form of a water insoluble calcium oxalate hydrate isolated, after oven drying at 100° C., as calcium oxalate monohydrate. The product obtained is referred to herein simply as "calcium oxalate".

In the event that the solution of mixed acids has been obtained by the above noted procedure for the hydrolytic conversion of di- and tricarboxy cellulose to a mixed acid product using sulfurous acid as a catalyst, the reaction product of the hydrolysis first is concentrated by boiling until substantially all of the sulfurous acid has been removed. Water then is added in amount sufficient to provide an acid solution having a concentration such that during the subsequent precipitation reaction and at the critical pH range employed the calcium oxalate will remain undissolved and is recovered substantially completely, whereas the tartaric, glyoxylic and erythronic acids and their calcium salts remain completely in solution. The concentration at which this occurs obviously will be dependent upon the temperature and the pH at which the precipitation is carried out.

The precipitation reaction by which the oxalic acid is converted to insoluble calcium oxalate preferably is carried out at room or ambient temperature. However, it may be carried out at any temperature below the level at which the calcium oxalate product has a substantial water solubility.

Calcium ion then is added to the solution in at least the stoichiometric amount required for the substantially complete conversion of the oxalic acid content of the solution to water insoluble calcium oxalate. In practice, a slight excess of calcium ion is thus added to insure complete precipitation of the calcium oxalate, while maintaining the solution substantially unsaturated with respect to tartaric acid, glyoxylic acid, erythronic acid and the calcium salts thereof.

The pH of the solution is adjusted to the critical value of from pH 0.9 to pH 2.0 preferably pH 0.9 to pH 1.7. As is indicated by the solubility curves presented in the drawing, calcium oxalate is precipitated almost quantitatively within this pH range, to the exclusion of the calcium salts of the other acids present in the solution.

The calcium ion may be provided in the form of any water soluble salt of calcium which does not contribute contaminating ions nor react adversely with the acid constituents of the reaction mixture. Suitable calcium salts accordingly comprise either slaked or unslaked lime, calcium chloride, calcium acetate or calcium carbonate which, though water insoluble per se, reacts with the oxalic acid present in the solution and thereby is converted to calcium oxalate. Slaked lime is preferred, since it also provides pH adjustment and supplies no undesirable anions to the reaction mixture.

Since the original solution is quite strongly acid and has a pH of about 1, the pH adjustment advantageously is effectuated contemporaneously with the addition of the calcium ion by the addition of lime to the stipulated pH value. However, if water soluble acid salts of calcium are employed as a source of calcium ion, the desired pH adjustment may be achieved either before or after the addition of such salts by the addition of the predetermined quantity of a suitable water soluble base such as sodium hydroxide or potassium hydroxide, or acids such as hydrochloric acid or acetic acid.

After the addition of calcium ion and pH adjustment, and if the concentration of calcium oxalate is low, then the solution preferably first is seeded with calcium oxalate. It then is permitted to stand for a time sufficient to insure complete precipitation of the calcium oxalate in a form in which it may be separated. Normally at least 1 to 3 hours should be allowed for this purpose. The precipitated calcium oxalate then is removed by filtration and washed. It may be converted to free oxalic acid by treatment with sulfuric acid, by ion exchange techniques, or otherwise in known manner.

Separation of Meso Tartaric Acid

The tartaric acid content of the reaction mixture is separated in the form of calcium meso tartrate dihydrate, which is converted to calcium meso tartrate monohydrate by oven drying at 100° C. The product obtained is referred to herein simply as "calcium tartrate".

The filtrate and washings remaining from the separation of the calcium oxalate contain tartaric, glyoxylic and erythronic acids in the form of the free acids and/or their calcium salts which at the pH of the solution are water soluble. The tartaric acid content of the solution next is separated by taking advantage of the selective insolubility of its calcium salt at a slightly elevated pH range.

This is accomplished by insuring that the concentration of the solution with respect to its various acid components is such as to permit substantially quantitative precipitation of calcium tartrate without exceeding the solubility limits of glyoxylic and erythronic acids and their calcium salts at the temperature of the reaction. Again it is preferred to carry out the precipitation reaction at room or ambient temperature.

The tartaric acid is removed by adding calcium ion in amount sufficient to convert it substantially completely to calcium tartrate, while maintaining the solution substantially unsaturated with respect to glyoxylic acid, erythronic acid and their calcium salts. This is accomplished in the manner described above, by adding a suitable water soluble salt of calcium, or a salt converted to water soluble condition upon contact with the acid components of the reaction mixture. Suitable calcium compounds for this purpose again comprise slaked or unslaked lime, calcium chloride, calcium acetate or calcium carbonate.

As shown in the calcium tartrate curve of the drawing, to effectuate the selective precipitation of the calcium tartrate the pH of the solution is adjusted to a value of from pH 2.8 to pH 4.4, preferably pH 3 to pH 4, in which range the calcium tartrate is precipitated selectively and almost quantitatively, without contamination by the calcium salts of glyoxylic or erythronic acids also present in the solution.

In the normal and preferred manner of proceeding, the calcium tartrate is precipitated by the addition of a further quantity of lime in the form of calcium hydroxide. Being basic, this material when added in the controlled and predetermined amount elevates the pH value of the solution to the desired range, thereby precipitating insoluble calcium tartrate.

Sufficient time is allowed to permit the calcium tartrate to precipitate completely and in a form in which it can be removed effectively from the solution. At least 1 hour, preferably 3 or 4 hours, should be allowed for this purpose. Thereafter the precipitated calcium tartrate is removed by filtering or centrifuging, and washed. It may be converted to free tartaric acid product in known manner by treatment with sulfuric acid, by ion exchange methods or otherwise.

Separation of Glyoxylic Acid

The glyoxylic acid also is separated in the form of its calcium salt (calcium glyoxylate hemihydrate, after oven drying at 100° C., referred to herein simply as "calcium glyoxylate"), but at a still more elevated pH range.

To achieve this result the filtrate and washings remaining from the separation of the calcium tartrate are concentrated by evaporation to a level at which their glyoxylic acid content upon the addition of calcium ion will precipitate as calcium glyoxylate. This will occur when they contain from 4 to 20% by weight of glyoxylic acid.

Calcium ion then is added in at least the stoichiometric amount required for the conversion of the glyoxylic acid to calcium glyoxylate without exceeding the solubility of the calcium salt of erythronic acid, which also is present in the solution. Again the calcium ion preferably is added in the form of a calcium compound such as lime (slaked or unslaked), calcium chloride, calcium acetate or calcium carbonate.

Before, contemporaneously with, or subsequently to the addition of the calcium ion, the pH of the solution is adjusted to the critical level required for the selective precipitation of the calcium glyoxylate. This level is critical in the present instance not only from the standpoint of insuring complete precipitation of the desired calcium glyoxylate product, but also from the standpoint of preventing the undesired conversion of glyoxylic acid by the Cannizzaro reaction to oxalic acid and glycolic acid.

Both of these objectives are achieved by adjusting the pH of the solution to a value of from 4.5 to 5.4, preferably 4.5 to 5.0. As shown in the calcium glyoxylate curve of the drawings, within this pH range the calcium glyoxylate is precipitated almost quantitatively to the exclusion of the calcium erythronate, and to the exclusion of the occurrence of the above noted Cannizzaro reaction.

In the normal and preferred manner of proceeding, this pH level is achieved by the addition of calcium hydroxide to the reaction mixture until the desired pH level has been reached. Where a calcium salt other than lime is employed, it may be necessary to adjust the pH to the necessary level by the addition of a controlled amount of another base such as sodium hydroxide or potassium hydroxide.

To permit complete precipitation of the calcium glyoxylate, the reaction mixture should be permitted to stand for at least three hours, preferably for 16 to 24 hours. Thereafter the precipitated calcium glyoxylate is filtered off, washed with water, and, if desired, converted to glyoxylic acid in known manner.

Separation of Erythronic Acid

The filtrate and washings comprising the solution remaining from the foregoing fractionation process whereby the oxalic, tartaric and glyoxylic acids have been removed as their calcium salts, contain predominantly erythronic acid in the form of its water soluble calcium salt, together with trace amounts of the calcium salts of oxalic, tartaric and glyoxylic acids. Certain amounts of inorganic materials deriving from the added precipitating and pH-adjusting reagents also may be present. However, if lime or calcium carbonate have been used as the source of calcium ion, such extraneous inorganic materials are largely absent and the solution may be decationized by ion exchange procedures to give a solution of substantially pure erythronic acid in a condition in which it is applicable to the various commercial uses of that product.

EXAMPLES

The process of the invention for the separation of oxalic, tartaric, glyoxylic and erythronic acids from aqueous solutions containing the same, is illustrated further in the following examples.

EXAMPLE 1

The mixture of organic acids which was the starting material for the fractionation process of the invention was obtained by placing 8.47 grams of tricarboxy cellulose and 100 ml. of 6.35% by weight sulfurous acid aqueous solution in a 250 ml. stainless steel sealed bomb. The tricarboxy cellulose had a 62.40% carboxyl content and contained 2.8219 carboxyl groups per glucose unit. This corresponded to a dicarboxy cellulose content of 17.81% by weight and a tricarboxy cellulose content of 82.19% by weight.

The bomb and its contents were heated at 115° C. for 16 hours. The resulting reaction mixture was evaporated at 45° to 50° C. under vacuum to a thick syrup, thereby removing the excess sulphur dioxide. The syrup was redissolved in 200 ml. water followed by stirring with calcium hydroxide to a pH of 1.65.

The mixture then was seeded with a trace amount of calcium oxalate and permitted to stand at room temperature for three hours. The precipitated calcium oxalate was removed by filtration, and dried to 100° C. to a constant weight of 0.205 grams.

To the filtrate and washings remaining after the removal of the calcium oxalate, calcium hydroxide was added with stirring to a pH of 3.4 to 3.6. The mixture was permitted to stand at room temperature for three hours. The precipitated calcium tartrate was collected on a filter, washed, and oven dried at 100° C. to a constant weight of 7.1391 grams, i.e. the quantitative amount within the limits of experimental error.

To convert the precipitated calcium tartrate product to tartaric acid, the calcium tartrate was decationized over a strong cation exchange resin (Amberlite). The aqueous solution, 400 ml., was evaporated to a syrup under vacuum at 45° C. The syrup crystallized after seeding with a trace of tartaric acid. The white crystals were air dried, followed by oven drying to a constant weight of 5.1037 grams, 99.8% of theory. The product melted at 156°–159° C. The mixed melting point with anhydrous meso tartaric acid was 155°–59° C.

Next, the hydrolysate remaining after removal of the calcium tartrate was acidified to a pH of 2 by the addition of 2% hydrochloric acid. The resulting light brown solution was concentrated under vacuum. Calcium hydroxide was added with stirring until the pH of the mixture was 4.0 to 5.0, thereby precipitating calcium glyoxylate.

The reaction mixture was permitted to stand at room temperature for from 20 to 24 hours. The precipitated calcium glyoxylate was collected on a filter and washed with four portions of 5 ml. each cold water to remove color. After oven drying, the remaining white solid weighed 3.9912 grams, or 94.01% of theory.

The filtrate was further concentrated to 25 ml. in the same manner and permitted to stand at room temperature for an additional three days. This yielded an additional quantity of 0.2765 grams of calcium glyoxylate, or a total yield of 100.52% of theory.

The remaining filtrate contained the calcium erythronate content of the original solution in a completely dissolved condition.

EXAMPLE 2

This example illustrates the selective precipitation of calcium oxalate from complex solutions containing the same at controlled pH.

Portions of oxalic acid dihydrate (Bakers reagent grade) were dissolved in 30 ml. water. 10 ml. of 13.20% calcium chloride solution was added with stirring. The pH of the resulting solution was adjusted to the desired pH value by the addition of hydrochloric acid and/or sodium hydroxide while stirring. In making this adjustment the upper pH values were measured by using a standard pH meter, while the lower pH values, i.e. those below pH 1.5, were measured using "Hydrion" pH paper having a range of from pH 0 to pH 1.5.

The reaction mixtue was permitted to stand at room temperature for 16 hours after which the calcium oxalate product was oven dried to constant weight at 100° C. The experimental conditions and results are shown in the following table.

| Weight of Oxalic Acid (g) | pH of the solution | | Calcium oxalate monohydrate | | Yield (%) |
|---|---|---|---|---|---|
| | At start | At 20 hrs | Theory(g) | Actual yield(g) | |
| 0.9744 | 0.01 | 0.10 | 1.1291 | 0.6908 | 61.18 |
| 0.9135 | 0.20 | 0.42 | 1.0585 | 1.0317 | 97.47 |
| 1.0123 | 0.40 | 0.55 | 1.1730 | 1.1491 | 97.96 |
| 0.9262 | 0.55 | 0.65 | 1.0732 | 1.0499 | 97.82 |
| 0.9262 | 0.80 | 0.90 | 1.0732 | 1.0696 | 99.66 |
| 0.9262 | 1.35 | 1.45 | 1.0732 | 1.0730 | 99.98 |
| 0.9262 | 1.75 | 1.85 | 1.0732 | 1.0946 | 101.99 |
| 0.9262 | 4.30 | 4.30 | 1.0732 | 1.0820 | 100.81 |

The foregoing values establish that within the critical pH range of pH 0.4 to pH 2.0, preferably pH 0.9 to pH 1.7, calcium oxalate is precipitated from aqueous solutions in which it is contained selectively and quantitatively. The values are used in plotting the calcium oxalate graph of the drawings.

EXAMPLE 3

This example illustrates the selective precipitation of calcium tartrate from aqueous solutions contaiing the same at various pH levels.

Samples of meso tartaric acid monohydrate (Aldrich Chemical Co., 99% pure) were dissolved in 30 ml. portions of water. 0.50 Gram calcium chloride was added to each and the pH of the resulting mixture adjusted to the values indicated in the table below. The pH of each solution was adjusted to the indicated level by the addition of sodium hydroxide solution in 1% and 10% concentrations. The indicated pH values were kept constant by adding dilute 1% sodium hydroxide. In each case the system was filtered after standing overnight. The precipitated calcium meso tartrate was dried to constant weight in an oven at 100° C. The conditions and results for each experiment are shown in the table below.

| Weight of meso tartaric acid monohydrate (g) | pH of the solution | Calcium meso tartrate monohydrate | | |
|---|---|---|---|---|
| | | Recovered(g) | Theory (g) | % |
| 0.5013 | 1.75 | — | 0.6085 | -0- |
| 0.5013 | 1.85 | — | 0.6085 | — |
| 0.5013 | 2.00 | 0.0459 | 0.6085 | 7.54 |
| 0.5038 | 2.50 | 0.4982 | 0.6116 | 81.46 |
| 0.5000 | 3.00 | 0.5900 | 0.6069 | 97.22 |
| 0.5013 | 3.25 | 0.6017 | 0.6085 | 99.00 |
| 0.5013 | 3.50 | 0.6048 | 0.6085 | 99.39 |
| 0.5000 | 4.00 | 0.5941 | 0.6069 | 97.89 |
| 0.5017 | 4.50 | 0.6059 | 0.6090 | 99.49 |

The foregoing results, as plotted in the calcium tartrate curve of the drawings, indicate that calcium tartrate is precipitated selectively and quantitatively from aqueous solutions of tartaric acid at a pH range of from 2.8 to 4.4, preferably pH 3 to pH 4.

EXAMPLE 4

This example illustrates the critical pH range over which calcium glyoxylate hemihydrate is precipitated from aqueous solutions of glyoxylic acid.

A glyoxylic acid solution, (50%, BASF Corp.,) 2.00 g., and 1.125 g. calcium chloride (1.5 mole per mole glyoxylic acid) in 25 ml. aqueous solution was adjusted to pH 1.20 by the addition of calcium hydroxide powder while stirring. The solution was seeded with calcium oxalate and the precipitate (trace amount) was removed by filtration after standing for two hours at room temperature.

The pH of the solution was adjusted to the selected value by the addition of 2% sodium hydroxide. It then was allowed to stand at room temperature for three days. The resultant white precipitate was recovered by filtration and dried in a vacuum desiccator over calcium chloride for 24 hours.

The above procedure was repeated, changing the pH conditions each time, with the results shown in the table below.

| pH of the Solution | Calcium Glyoxylate . ½ $H_2O$ Recovered | |
|---|---|---|
| | (g) | % |
| 1.60 | 0.0082 | 0.59 |
| 2.20 | 0.1129 | 8.19 |
| 2.80 | 0.7283 | 52.84 |
| 3.25 | 1.0526 | 76.36 |
| 4.50 | 1.2007 | 87.11 |
| 5.00 | 1.2210 | 88.58 |
| 5.40 | 1.2673 | 91.94 |
| Theory | 1.3783 | 100.00 |

The foregoing values establish that within the critical pH range of pH 4.5 to pH 5.4, preferably pH 4.5 to pH 5.0, calcium glyoxylate is precipitated almost quantitatively from solutions in which it is contained. The values, corrected for the solubility of calcium glyoxylate hemihydrate in water, are used in plotting the calcium glyoxylate graph of the drawings.

Having thus described our invention in preferred embodiments, we claim:

1. The process for separating oxalic, tartaric, glyoxylic and erythronic acids from aqueous solutions containing the same, comprising:
   a. adding calcium ion to the solution in at least the stoichiometric amount required for the substantially complete conversion of the oxalic acid content thereof to calcium oxalate, while maintaining the solution substantially unsaturated with respect to tartaric acid, glyoxylic acid, erythronic acid and the calcium salts thereof,
   b. adjusting the pH of the solution to a value of from pH 0.9 to pH 2.0, thereby precipitating insoluble calcium oxalate,
   c. removing the precipitated calcium oxalate from the solution,
   d. adding a further quantity of calcium ion to the resulting substantially calcium oxalate-free second solution in at least the stoichiometric amount required for the substantially complete conversion of the tartaric acid content thereof to calcium tartrate, while maintaining the second solution substantially unsaturated with respect to glyoxylic acid, erythronic acid and the calcium salts thereof,
   e. adjusting the pH of the second solution to a value of from 2.8 to 4.4, thereby precipitating insoluble calcium tartrate,
   f. removing the precipitated calcium tartrate from the second solution,
   g. concentrating the resulting third solution,
   h. adding calcium ion to the resulting substantially calcium oxalate-free and calcium tartrate-free third solution in at least the stoichiometric amount required for the substantially complete conversion of the glyoxylic acid content thereof to calcium glyoxylate, while maintaining the third solution substantially unsaturated with respect to erythronic acid and the calcium salt thereof,
   i. adjusting the pH of the third solution to a value of from 4.5 to 5.4 thereby precipitating calcium glyoxylate, and
   j. separating the precipitating calcium glyoxylate from the third solution, thereby providing a residual solution comprising a water solution of erythronic acid and its calcium salt.

2. The process of claim 1 wherein the calcium ion is provided by the addition of calcium oxide.

3. The process of claim 1 wherein the calcium ion is provided by the addition of calcium hydroxide.

4. The process of claim 1 wherein the calcium ion is provided by the addition of calcium carbonate.

5. The process of claim 1 wherein the calcium ion is provided by the addition of calcium chloride.

6. The process of claim 1 wherein the calcium ion is provided by the addition of calcium acetate.

7. The process of claim 1 including the step of adjusting the pH of the first solution to a value of from pH 0.9 to pH 1.7 for the precipitation of the calcium oxalate.

8. The process of claim 1 including the step of adjusting the pH of the second solution to a value of from pH 3 to pH 4 for the precipitation of calcium tartrate.

9. The process of claim 1 including the step of adjusting the pH of the third solution to a value of from pH 4.5 to pH 5.0 for the precipitation of calcium glyoxylate.

10. The process of claim 1 including the step, preliminary to the precipitation of calcium glyoxylate therefrom, of concentrating the third solution to a level at which it contains from 4% to 20% by weight of glyoxylic acid.

11. The process for separating oxalic, tartaric, glyoxylic and erythronic acids from aqueous solutions containing the same, comprising:
   a. adding lime to the solution in at least the stoichiometric amount required for substantially complete conversion of the oxalic content thereof to calcium oxalate while maintaining the solution substantially unsaturated with respect to tartaric acid, glyoxylic acid, erythronic acid and the calcium salts thereof,
   b. adjusting the pH of the solution to a value of from pH 0.9 to pH 1.7, thereby precipitating insoluble calcium oxalate,
   c. separating the precipitated calcium oxalate from the solution,
   d. adding lime to the resulting second solution in at least the stoichiometric amount required for the substantially complete conversion of the tartaric acid content thereof to calcium tartrate while maintaining the second solution substantially unsaturated with respect to glyoxylic acid, erythronic acid and the calcium salts thereof,
   e. adjusting the pH of the second solution to a value of from pH 3 to pH 4 thereby precipitating insoluble calcium tartrate,
   f. separating the precipitated calcium tartrate from the second solution,
   g. concentrating the resulting third solution to a glyoxylic acid content of from 4 to 20% by weight,
   h. adding lime to the resulting concentrated third solution in at least the stoichiometric amount required for the substantially complete conversion of the glyoxylic acid content thereof to calcium glyoxylate while maintaining the third solution substantially unsaturated with respect to erythronic acid and the calcium salt thereof,
   i. adjusting the pH of the third solution to a value of from 4.5 to 5.0 thereby precipitating calcium glyoxylate, and
   j. separating the precipitated calcium glyoxylate from the resulting aqueous solution of erythronic acid.

12. The process of separating oxalic acid from an aqueous solution containing oxalic acid and at least one member of the group consisting of tartaric acid, glyoxylic acid and erythronic acid, comprising:
   a. adding calcium ion to the solution in at least the stoichiometric amount required for the substantially complete conversion of the oxalic acid content thereof to calcium oxalate while maintaining the solution substantially unsaturated with respect to the residual acids contained therein,
   b. adjusting the pH of the solution to a value of from pH 0.9 to pH 2.0, thereby precipitating insoluble calcium oxalate and
   c. removing the precipitated calcium oxalate from the solution.

13. The process of claim 12 wherein calcium ion is added to the solution in the form of lime and wherein the precipitation of the resulting calcium oxalate is effectuated at a pH of from pH 0.9 to pH 1.7.

14. The process of separating tartaric acid from aqueous solutions containing tartaric acid and at least one member of the group consisting of glyoxylic acid and erythronic acid, the process comprising:
   a. adding calcium ion to the solution in at least the stoichiometric amount required for the substantially complete conversion of the tartaric acid content thereof to calcium tartrate while maintaining the solution substantially unsaturated with respect to glyoxylic acid and erythronic acid and the calcium salts thereof,
   b. adjusting the pH of the solution to a value of from pH 2.8 to pH 4.4 thereby selectively precipitating insoluble calcium tartrate and
   c. removing the precipitated calcium tartrate from the solution.

15. The process of claim 14 wherein the calcium ion is added to the solution in the form of lime and the precipitation of the calcium tartrate is carried out at a pH of from pH 3 to pH 4.

16. The process of separating glyoxylic acid from solutions containing glyoxylic and erythronic acids, the process comprising:
   a. establishing in the solution a concentration of glyoxylic acid sufficiently great to precipitate calcium glyoxylate upon the addition of calcium ion,
   b. adding calcium ion to the solution in at least the stoichiometric amount required for the substantially complete conversion of the glyoxylic acid content thereof to calcium glyoxylate while maintaining the solution substantially unsaturated with respect to erythronic acid and the calcium salt thereof,
   c. of adjusting the pH of the solution to a value of from pH 4.5 to pH 5.4, thereby precipitating calcium glyoxylate, and
   d. separating the precipitated calcium glyoxylate from the solution.

17. The process of claim 16 including the step of providing a solution containing from 4% to 20% by weight glyoxylic acid, adding the calcium ion in the form of lime, and precipitating the calcium glyoxylate at a pH of from pH 4.5 to pH 5.0.

* * * * *